United States Patent [19]

Philipot

[11] Patent Number: 5,300,098

[45] Date of Patent: Apr. 5, 1994

[54] PATIENT WARMER HEATER BLOWER CONTROL

[75] Inventor: Thomas H. Philipot, Jackson, Mich.

[73] Assignee: Progressive Dynamics, Inc., Marshall, Mich.

[21] Appl. No.: 883,942

[22] Filed: May 14, 1992

[51] Int. Cl.$^5$ .......................... A61F 7/00; H05B 1/02
[52] U.S. Cl. ........................ 607/96; 607/107; 607/108; 219/482; 219/527
[58] Field of Search ............. 128/399, 400, 402, 24.1, 128/736; 606/32, 31, 27; 219/487, 489, 490, 412, 527, 528, 212; 165/46; 607/96, 104, 107, 108

[56] References Cited

U.S. PATENT DOCUMENTS

| | | | |
|---|---|---|---|
| 4,587,959 | 5/1986 | Ruderian | 128/400 |
| 4,819,656 | 4/1989 | Spector | 128/736 |
| 4,844,072 | 7/1989 | French et al. | 128/400 |
| 4,867,230 | 9/1989 | Voss | 128/402 |
| 5,044,364 | 9/1991 | Crowther | 128/400 |
| 5,097,829 | 3/1992 | Quisenberry | 128/400 |
| 5,125,238 | 6/1992 | Ragan et al. | 62/259.3 |
| 5,165,400 | 11/1992 | Berke | 128/400 |
| 5,184,612 | 2/1993 | Augustine | 128/400 |

Primary Examiner—Jessica J. Harrison
Attorney, Agent, or Firm—Beaman & Beaman

[57] ABSTRACT

A hypothermic therapy heater blower control system for use with patient warming blankets flowing warm air over the patient wherein the control system includes a data display indicating the temperature of the supplied air and the circuitry includes audible and visual alarms to indicate overheating or failure modes. The circuitry includes dual safety heater shut-off circuits and also includes a self-testing cycle which tests all of the major safety features and shut-offs, and in the test mode the circuitry simulates an over temperature condition.

12 Claims, 2 Drawing Sheets

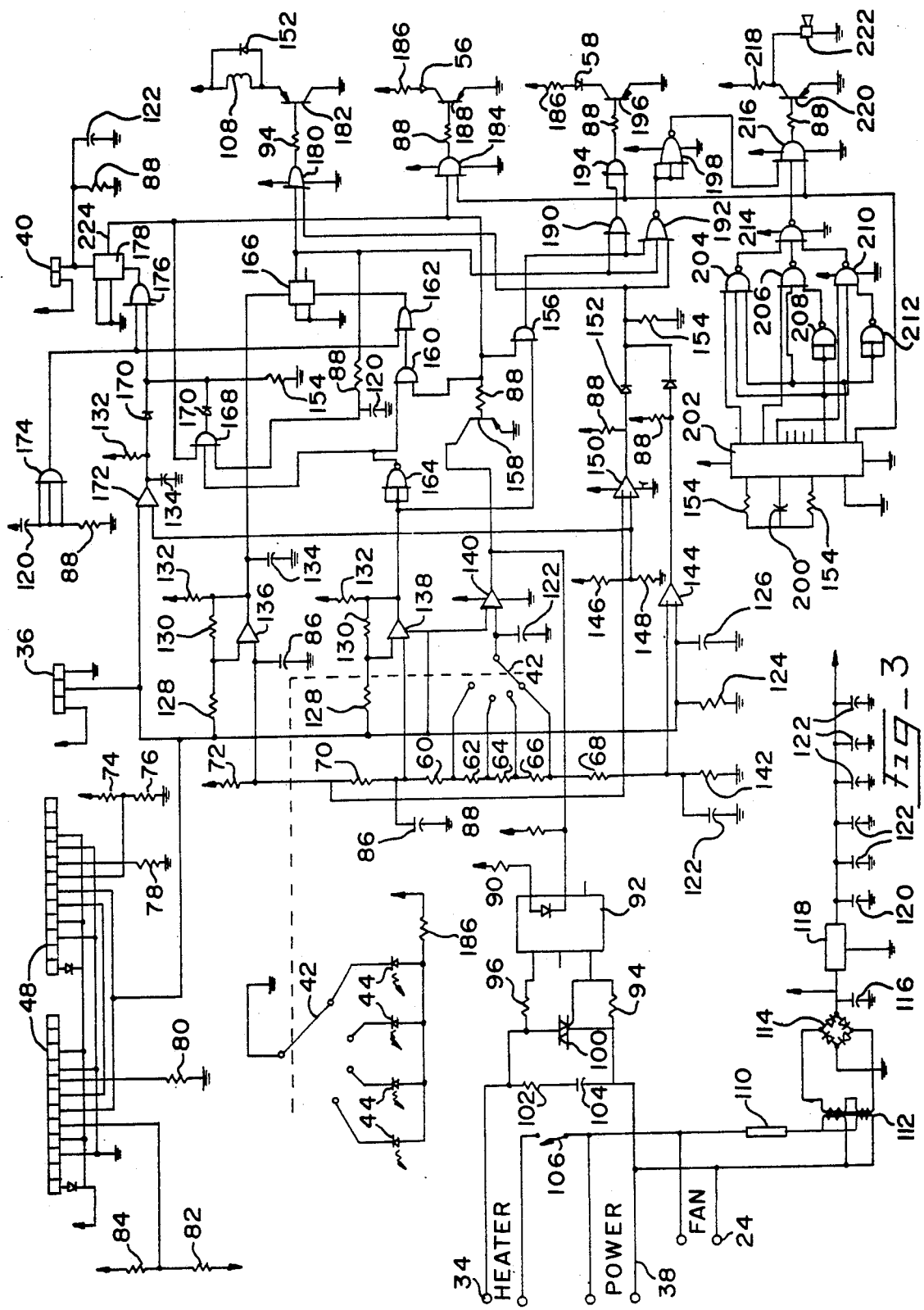

PATIENT WARMER HEATER BLOWER CONTROL

BACKGROUND OF THE INVENTION

1. Field of the Invention

The invention pertains to patient warmer heater blower control systems wherein hot air is distributed over the patient's body through an air pervious blanket, the circuitry controlling the temperature of the air utilizes several safety features to prevent overheating and a self-test cycle to simulate overheating for testing operational characteristics.

2. Description of the Related Art

Hypothermic therapy systems are used to return the patient to a normal body temperature after surgery, shock, immersion in water, or the like. In such instances, it is necessary to bathe the patient's body in warm air to return the body temperature to normal.

Known hypothermic therapy devices include inflatable envelopes or blankets placed above, below, or around the patient's body having small orifices directed toward the patient whereby the warm air is directly applied to the patient. As the temperature of the air being imposed upon the patient must be closely regulated and predetermined, a control system for the apparatus supplying the heated air must include accurate temperature regulation features to prevent overheating of the patient which could inflict serious injury or even be fatal.

While it is known to use thermostatic controls with air heaters utilizing electric resistant heating elements, such thermostatic controls simply sense the temperature of the gas, air or adjacent apparatus, and in the event of malfunction the circuitry is not self-analyzing and overheating may occur.

Known hypothermic therapy systems using electric resistant heaters to heat air do not employ temperature indicators to assess the actual temperature of the air being supplied and do not employ dual safety circuits to de-energize the heater element and do not employ self-testing circuits for determining the operability of the circuit safety features, and the possibility for malfunctioning exists in presently available systems.

SUMMARY OF THE INVENTION

It is an object of the invention to provide a hypothermic therapy heater system for use with an inflatable air pervious blanket wherein an air supply fan, air filter, air heater, and electronic control circuit for the heater is concisely mounted within a common housing which is pedestal mounted.

Another object of the invention is to provide a patient warmer heater blower control circuit for electric heater elements wherein the desired temperature of the blanket air is set by the operator, and the actual temperature of the air being supplied to the blanket is electronically indicated and controlled.

A further object of the invention is to provide a hypothermic therapy air temperature control system wherein the circuitry includes both audio and visual alarm systems, and wherein the audio alarm emits a variable sound frequency to permit operators having limited audio ranges of discernability to be warned, and produces a distinctive, immediately recognizable sound pattern.

Yet another object of the invention is to provide a hypothermic therapy air temperature control system utilizing an electric resistant heater element wherein dual circuitry for controlling the energization of the heater element provides a safety redundancy eliminating the possibility of patient overheating.

An additional object of the invention i to provide a control circuit for a patient warmer blanket utilizing electrically heated air wherein the primary circuit includes a test circuit which may be initiated prior to normal operation of the apparatus to put the circuitry in an over temperature condition which, if the circuit is operating properly, will cause the electric resistance heater to be deactivated. Thereupon, the circuitry may be energized in the normal manner for usage with the assurance that the over temperature safety features are in good working order.

Preferably, the patient warmer heater blower control system disclosed in the instant application is used with the assignee's patient warming blanket as disclosed in U.S. Pat. No. 5,125,238 dated Jun. 30, 1992. In this patent the blanket constitutes a generally rectangular envelope defining a blanket adapted to be placed upon the body of a prone patient. The blanket is formed of a thermoplastic film material and the edges and ends thereof are heat sealed, and in a similar manner, the upper and lower blanket sides are heat sealed at staggered and spaced positions to control the blanket dimensions during inflation. A plurality of small orifices are defined in that side of the blanket disposed toward the patient, and this blanket side also includes a high friction air pervious surface to aid in maintaining the blanket upon the patient and for comfort and texture purposes. The heated compressed air is introduced into the blanket at the blanket end located adjacent the patient's feet, and a foldable fitting formed of paper or the like includes an orifice receiving the nozzle of the hose supplying the heated pressurized air. Preferably, the blanket is formed of low cost, easily manufacturable components permitting the blanket to be disposed of after a single use, and the folding nozzle receiving fitting permits the deflated blanket to be folded and concisely stored and packaged.

The heated pressurized air supply for the blanket is housed within a common pedestal mounted housing. Within the housing, a squirrel cage fan is located drawing air through a filter formed in a housing opening, and the fan discharges into a manifold containing an electric resistant type heat exchanger heating the discharged air. The manifold communicates with a housing outlet fitting, and a flexible hose interconnects the housing fitting and the blanket fitting to establish a connection between the fitting and blanket.

The electronic circuit for controlling the fan and electric heat exchanger element is located within the housing, and upon an exterior control panel of the housing, control switches, indicating lights and indicia ar located for conveniently operating the blanket and observing the temperature of the pressurized air being supplied to the blanket by the fan.

The control circuitry includes a manually positionable rotary switch for presetting the desired temperature of the air to be supplied to the blanket. In the disclosed embodiment, four different air temperatures may be selected, and an LED linear bar display is mounted upon the housing visible to the operator wherein the temperature of the air is indicated by the length of a bar defined by a plurality of LEDs and the operator may determine at a glance if the temperature of the air being supplied to the blanket is as preselected.

A sensor located within the heat exchanger plenum continually senses the temperature of the air therein and controls the circuit energizing the heat exchanger electric resistance element to maintain the air temperature within the plenum as preselected, and the heat exchanger element is cycled between on and off conditions to achieve the predetermined temperature.

The circuit includes safety features whereby if the air temperature becomes greater than the control set point, the electrical supply to the heat exchanger element is terminated. In such over temperature event, both an audible alarm and a flashing visual alarm are energized. The audible alarm consists of a plurality of sequentially emitted variable sound frequencies as to produce a distinctive sound for distinguishing the hypothermic therapy apparatus from other medical equipment that may be in the vicinity.

If the unit continues to heat the air within the plenum beyond the set limit, the audible alarm continues, the flashing light continues, and the heater element is de-energized through a secondary circuit system than that normally utilized when an over temperature condition is originally sensed. In such instance, the de-energized condition remains until the entire unit has been turned off manually and reset.

If the temperature sensor malfunctions, the alarms will energize, and the circuit will remove electrical power from the heater element. However, upon the sensor recovering from an open condition, the circuit will automatically reset. Sensor failure during operation also de-energizes the heater element and a failed shorted sensor will result in the alarms being energized and the heating element being switched off until manually reset. Sensor failures are fail-safe.

The operability of the safety aspects of the circuitry can be automatically tested prior to the hypothermic therapy system being used with a patient. The manual actuation of a "test" switch will place the circuitry in an over temperature condition from the preset temperature and cause the circuitry to automatically function to energize the alarms and de-energize the electric resistance element within the fan plenum. After the test cycle has been automatically completed, and the circuit is proven to be operable, the blanket may be placed upon the patient and the apparatus used in the normal manner.

BRIEF DESCRIPTION OF THE DRAWING

The aforementioned objects and advantages of the invention will be appreciated from the following description and accompanying drawings wherein:

FIG. 3 illustrates the electric circuitry used to control the heater elements and fan in accord with the concepts of the invention.

DESCRIPTION OF THE PREFERRED EMBODIMENT

Figure 1:
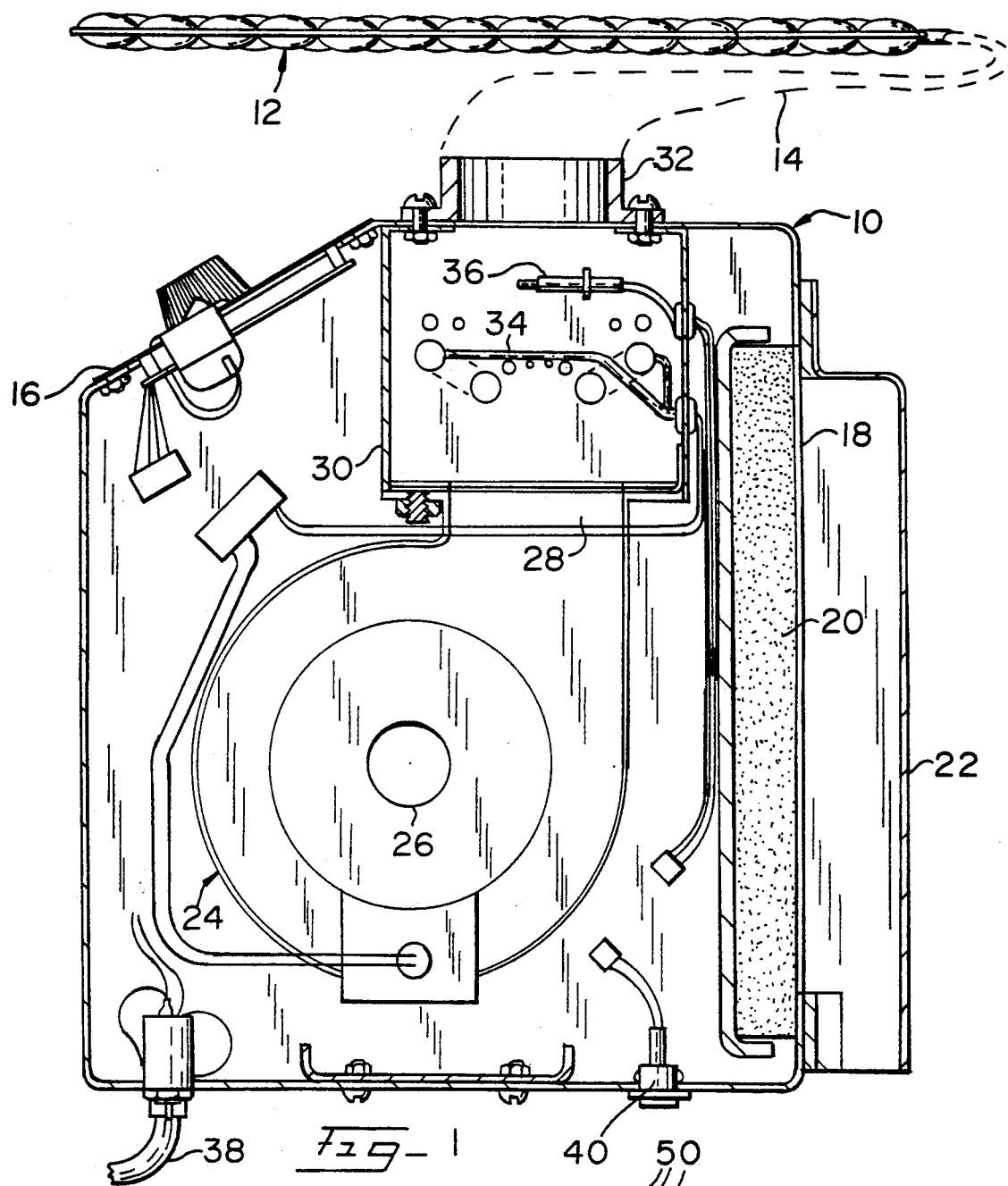
FIG. 1 is an elevational sectional view of the patient warmer heater blower control housing of the invention, the hose and blanket being shown in a schematic manner.
Figure 2:
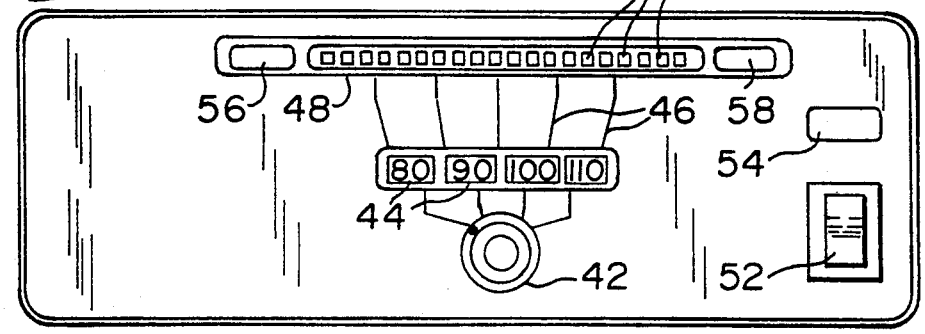
FIG. 2 is a plan view of the control panel portion of the housing.

With reference to FIGS. 1 and 2, the hypothermic therapy control system in accord with the invention includes a sheet metal housing 10 which is preferably mounted upon a pedestal support, not shown. The housing 10 includes the apparatus for supplying the heated pressurized air to the blanket distributor 12 which is air pervious, and preferably, is constructed in accord with assignee's U.S. Pat. No. 5,125,238. The housing 10 is connected to the blanket 12 by a flexible hose 14 illustrated in a schematic manner.

The housing 10 includes a control panel 16 preferably obliquely disposed to the vertical for ease of viewing, and as later described, the controls for the apparatus are mounted upon the panel 16.

An opening 18 is defined in the rear of the housing 10 and an air filter 20 is located within the opening 18 to filter the air entering the housing. The opening 18, and filter 20, are protected and enclosed by the sheet metal baffle 22 which is open at its lower end permitting air to flow into the baffle and through the filter.

An electric fan 24 is located within the housing 10, and this fan is preferably of the squirrel cage type. The fan includes a central inlet 26 communicating with the interior of the housing 10 whereby air entering the fan first passes through the filter 20. The fan includes an outlet port 28 which is in communication with the plenum 30, and it will be appreciated that the port 28 and plenum 30 constitute a discharge for the fan. An outlet fitting 32 is mounted upon the top of the housing 10 permitting the hose 14 to be attached thereto. The fitting 32 communicates with the plenum 30 whereby the air heated within the plenum passes through the fitting 32 into the hose 14 and into the blanket 12.

The air within the plenum 30 is heated by an electric resistance heater element 34, and the temperature of the air within the plenum 30 is sensed by the electronic sensor 36. Power is supplied to the interior of the housing 10 through the power supply cord 38, and a circuit test switch 40 is located in the bottom of the housing for testing the circuit as later described.

Various controls and indicia are mounted upon the control panel 16, FIG. 2, and these controls include a manually adjustable rotary switch 42 for pre-setting the circuit to provide the predetermined temperature of the air to be supplied to the blanket 12. The switch 42 includes a pointer or marker whereby the switch may be rotated to one of four positions wherein air of 80° F., 90° F., 100° F. or 110° F. may be supplied to the blanket 12. Upon adjustment of the rotary switch 42, the appropriate temperature indicator 44 will be illuminated by a light emitting diode.

The actual temperature of the air being supplied to the blanket is indicated by the light emitting diode display 48, and temperature reference lines 46 extend between the selected temperature indicators 44 and the display 48. The display 48 consists of a plurality of linearly arranged LEDs 50 which are progressively lit from the left to the right, FIG. 2, as the air temperature increases. The reference lines 46 permit the operator to quickly compare the temperature of the air being supplied to the blanket to that which has been preselected by the switch 42.

The power switch for the apparatus is mounted upon control panel 16 as indicated at 52, and the power pilot light 54 indicates when the electrical power is on. The display 48 includes a test light 56 to indicate energization of the test cycle, as later described, and a caution or warning light 58 is also included in the display.

With reference to FIGS. 1 and 2, the temperature switch 42 is turned to provide the desired air temperature to the blanket 12. The air being discharged by the fan 24 into the plenum 30 will be heated within the plenum by the resistance heater 34, and the sensor 36 will sense the temperature of the air entering the fitting 32 and blanket 12. The temperature of the air entering the fitting 32 will be indicated by the LEDs 50, for instance, if 80° F. is the desired air temperature the five LEDs 50 at the left of the display 48 will be illuminated. Upon rotating the switch 42 to the 90° F. setting, and upon the air within the plenum 30 attaining the predetermined temperature, the eight leftmost LEDs 50 will be illuminated indicating to the operator that the desired preselected air temperature has been achieved.

The circuit for controlling the energizing of the heater element 34 is illustrated in FIG. 3, and the heater element 34 will be alternately energized and de-energized to maintain the desired air temperature.

With reference to FIG. 3, the rotary switch 42 includes a set of contacts to selectively energize the temperature indicating diodes 44, and also includes a set of contacts which determine the predetermined air temperature and energization of the heater element 34, as controlled by the resistors 60, 62, 64 and 66 and associated circuitry. The triac 100 supplies power to the heater 34, and the contacts of the relay 106 will normally be closed.

The values of the various components of the circuit of FIG. 3 are set forth in the following chart:

| Reference | Value or Code |
| --- | --- |
| 60 | 249 Ohms |
| 62, 64 | 442 Ohms |
| 66 | 453 Ohms |
| 68, 76 | 2.87K Ohms |
| 70 | 64.9 Ohms |
| 72 | 4.99K Ohms |
| 74 | 2.15 Ohms |
| 78, 80 | 1.5K Ohms |
| 82 | 1.18K Ohms |
| 84 | 3.74K Ohms |
| 88 | 10K Ohms |
| 90 | 620 Ohms |
| 94 | 1K Ohms |
| 96 | 27 Ohms |
| 102, 186 | 39 Ohms |
| 124, 154 | 100K Ohms |
| 128 | 24.3K Ohms |
| 130 | 5.1M Ohms |
| 132 | 51.1K Ohms |
| 142 | 475 Ohms |
| 146 | 8.87 Ohms |
| 148 | 1.15K Ohms |
| 218 | 5.1K Ohms |
| 86, 122 | .1 uf |
| 104 | .01 uf |
| 116 | 1000 uf |
| 120 | 10 uf |
| 126 | 1 uf |
| 134 | 100 uf |
| 200 | 180 pf |
| 92 | MOC 3032 |
| 100 | Q40 15L5 |
| 112 | DPC-16-640 |
| 118 | MC 7812 |
| 136, 138, 140, 144 | LM 2901 |
| 150, 172 | LM 2903 |
| 152, 170 | IN 4148 |
| 156, 160 | CD 4081 |
| 158, 188, 196, 220 | PN 2222 |
| 162, 176, 180, 190 | CD 4071 |
| 164, 192, 198 | CD 4025 |
| 166, 178 | CD 4013 |
| 168, 174, 216 | CD 4073 |
| 182 | PN 3638 |
| 184, 194 | CD 4081 |
| 202 | CD 4060 |
| 204, 206, 208, 210, 212, 214 | CD 4023 |

With reference to FIG. 3, the display 48 is in two sections, and is commercially available and pre-wired, resistors 84/82 and 74/76 set the lower and upper calibration points of the display. The display is a voltage indicator sensitive to the voltage being supplied to the display by the sensor 36.

Under normal operating conditions, the triac 100 will open and close the circuit to the heater element 34 to cycle the heater element to produce the desired air temperature. However, as the heated air is being directly applied to the patient through the blanket 12 it is of utmost importance that the patient not be overheated in the event of a malfunctioning of the heater element control circuit. An alarm circuit is incorporated into the circuitry to immediately sense and bring attention to the fact that the air temperature is greater than that predetermined by switch 42.

The alarm system includes an audio horn or buzzer 222, and also includes the warning or caution light 58 mounted in the control panel 16. The buzzer 222 is the most effective way to indicate malfunctioning and attract the attention of the operator. To assure immediate awareness of the audio alarm the sound frequencies produced by the buzzer 222 sequentially vary, and in this manner the alarm signals will differ from the usual noises of medical apparatus and immediately attract the attention of nearby personnel.

The actuation of the alarm buzzer 222 is controlled by the oscillator divider integrate circuit 202 in association with the resistors 154 directly attached to circuit 202 along with capacitor 200. The circuit 202 generates six discreet frequencies and these frequencies are combined in NAND gates 204, 206, 208, 210 and 212 to form a three frequency stepped output to drive the buzzer 222. AND gate 216 is used to enable this signal which is buffered through transistor 220. This alarm is triggered if any of four conditions occur.

The comparator 144 detects a temperature sensor voltage less than 0.120 volts enabling gate 192 and the buzzer circuit. This alarm would occur when the sensor 36 failed open or short circuited to ground.

The buzzer 222 will also be activated if comparator 136 detects a temperature sensor voltage greater than 1.260 volts, which represents a temperature of 126° F., comparing voltage set by the divider network, for greater than the time constant of resistor 132 and capacitor 134, and sets the output of flip-flop circuit 166 which enables gate 192 and the buzzer circuit. This alarm would be associated with the sensor 36 short circuiting to the +12 volt supply or an over temperature condition, i.e. greater than 1.260 volts from the sensor 36. A time constant is used because a false over temperature condition could occur for a short period if the unit has been running at a control temperature and is turned off. In such instance the temperature within the plenum 30 will momentarily rise due to residual heat, and the unit will read high for a few seconds as the fan carries away residual heat.

The buzzer 222 will also be energized if the comparator 138 detects a temperature sensor voltage greater than 1.245 volts, which represents a temperature of 124.5° F. As the AND gate 156 will be energized the unit is in the test mode as determined by the output of circuit 178. AND gate 156 enables gate 192 and energizes the alarm circuit. This alarm would be associated with normal operating parameters during the test sequence as described below.

The comparator 150 detects a voltage divider fault such as an open resistor 70, 60, 62, etc. which would cause the divider string reference voltage to disrupt the normal operation of the control circuit. When the divider voltage between resistors 70 and 72 exceeds the reference voltage (1.38) set by resistors 146 and 148, gate 192 will be enabled and activate the buzzer circuit.

The visual flash alarm or caution light 58 is triggered by gate 190 when either of the second or third faults discussed above occur. The flash rate of the warning light 58 is controlled by AND gate 194 and the output of the oscillator divider circuit 202. Transistor 196 is the power driver for this light.

To further improve the safety aspect of the control circuit, a self-testing of the control circuit is possible by momentarily closing the test circuit switch 40. The purpose of the self-test circuitry is to test the reaction of the circuit under "over temperature" conditions, i.e. when the temperature of the air within plenum 30 is greater than the preselected temperature as set by switch 42. At initial energization of the unit, capacitor 120, resistor 88 immediately below capacitor 120 and AND gate 174 generate a reset pulse to set the test mode flip-flop circuit 178 and the safety override flip-flop circuit 166 to their normal conditions. When the test button 40 is momentarily closed, the following sequence occurs.

Pin 224 of circuit 178 is set high. The test mode indicator light 56 starts to flash as driven by the circuit 178 output and the flash rate is set by the output of oscillator circuit 202 along with the output of AND gate 184 and power driver transistor 188. The safety override flip-flop 166 is held in the reset mode due to the inputs on circuits 160 and 162, the output of 166 is low. Assuming the temperature sensor 36 and other components are working properly, comparator 140 is in a high impedance state and the outputs of comparators 144 and 150 are low. Thus, the output of gate 180 is low, transistor 182 is biased to the on position, and safety interlock relay 106 as controlled by the relay coil 108 is closed allowing power to flow to the heater element 34 if the triac 100 is on. When transistor 158 is turned on, as caused by flip-flop 178 output being high, the triac driver optical coupler 92 will be turned on and the triac 100 will be on applying full power to the heater element 34. This simulates uncontrolled power to the heater element.

The temperature being sensed by sensor 36 will start to rise as air temperature throughout the plenum rises. When the 124.5° F. temperature comparator 138 trips (high) AND gate 156 turns on, causing over temperature indicator 58 to flash and the buzzer 222 to be energized. The output of gate 164 goes low along with the output of AND gates 160 and 162 removing the forced reset on circuit 166.

The heater element 34 continues to be energized and the output of sensor 36 continues to rise. The 126° F. temperature comparator 136 trips high, and after a short time delay as set by resistor 132 and capacitor 134, circuit 166 output is set high and this causes gate 180 to turn on, transistor 182 turns off, and the relay coil 108 will be turned off opening the contacts of relay 106 removing power from the heater element 34. Thereupon, the air temperature and the output of the sensor 36 will start to fall.

The 126° F. temperature comparator 136 trips low and the safety override flip-flop circuit 166 is no longer in a forced set condition. The temperature and temperature sensor outlet continue to fall.

At 124.5° F. temperature comparator 138 trips low. Gate 164 along with AND gates 160 and 162 turn on, forcing a reset of circuit 166. Circuit 166 output goes low, gate 180 goes low, and transistor 182 turns back on along with relay 106 as operated by coil 108. The contacts of relay 106 close allowing triac 100 to control power to the heater element 34. AND gate 156 is also turned off, which in turn disables the warning flasher 58 and the audio buzzer 222. AND gate 168 is also turned on for a short period. This turns on gate 176, resetting the test mode flip-flop circuit 178, which will disable the "TEST" lamp 56 and turn off transistor 158. The triac 100 and the triac control circuit are now no longer latched on.

The primary control comparator 140 will return the system to the same control point as the unit was in prior to activating the test sequence.

It will be appreciated that the above described circuit has four safety levels or functions:

First, the comparator 140 will turn off the triac driver 92 and triac 100, thus removing power from the heater element 34. This occurs any time that the temperature sensed by the temperature sensor 36 exceeds the set temperature, i.e. the reference voltage, selected by the temperature switch 42.

Secondly, if the normal controller was unable to prevent a temperature rise above 126° F., comparator 136 will trip high, set safety override flip-flop circuit 166, causing the warning lamp 58 to blink and the audio buzzer 222 to sound.

Thirdly, the above occurrence will also turn on gate 180, turn off transistor 182, and deactivate relay 106. The relay contacts of relay 106 will open and prevent power from flowing to the heater element 34. Since the over temperature condition occurred when the unit was not in the test mode, AND gate 160 prevents the caution override flip-flop circuit 166 from being reset. This will prevent the element 34 from receiving power until the unit is turned off and then back on again to reset the system. The caution or warning lamp 58 and the buzzer 222 will continue to operate until the unit is turned off.

Fourthly, if the relay coil 108 and associated contacts 106 fail to open during this test sequence and power continues to flow to the heater element 34, the temperature as sensed by temperature sensor 36 will continue to rise. When this temperature exceeds 135° F., comparator 172 will go high, or gate 176 will go high and reset test flip-flop 178. This will remove the unit from the test mode and remove the simulated fault, allowing the triac 100 to control power to the heater. This event would be treated as an abnormal over temperature condition and the actions discussed in the second and third situations above would occur.

If the temperature sensor 36 is defective, and is open, the comparator 144 detects a temperature sensor voltage less than 0.120 volts (comparing voltage set by the divider network defined by resistors 72, 70, 60, 62, 64, 66 and 68,) enabling gate 192 and the buzzer circuit to energize alarm 222. This alarm is associated with a sensor that failed because of an open circuit, failed due to a short circuit to ground, or has become disconnected. In addition, this mode will turn on gate 180, turn off transistor 182 and relay coil 108 will turn off. The relay contacts 106 will open and no electrical power will be allowed to flow to the heater element 34.

It will be appreciated that the above described redundant circuit eliminates the possibility of malfunctioning such that excessively hot air will be supplied to the blanket 12, and by controlling the heater element 34 by both the triac 100 and the relay 106 a fail-safe circuit is achieved which will prevent injury.

It is appreciated that various modifications to the inventive concepts may be apparent to those skilled in the art without departing from the spirit and scope of the invention.

I claim:

1. A hypothermic therapy control system for supplying heated pressurized air to a patient associated distributor comprising, in combination, a housing having a control panel, a fan within said housing having an air inlet and an air outlet, a plenum within said housing in communication with said fan outlet, an air inlet defined in said housing in communication with said fan inlet, an electric heater element within said plenum, a heated air outlet in communication with said plenum receiving heated air therefrom, an electronic control circuit within said housing operatively connected to said heater element adapted to selectively energize and de-energize said element, an adjustable rotary temperature control switch mounted on said housing control panel included in said control circuit adapted to preselect the air temperature within said plenum by rotation thereof to predetermined settings, and a plenum air temperature indicator comprising a plurality of light emitting diodes arranged in a linear pattern defining a light bar indicator mounted upon said control panel indicating the temperature of the air within said plenum and a plurality of reference indicia lines extending between said control switch and subsets of light emitting diodes along said light bar indicator to define temperature ranges which facilitate visual comparison between the temperature selected by said switch and the actual air temperature within said plenum.

2. In a hypothermic therapy system as in claim 1, said heated air outlet comprising a fitting defined in said housing in communication with said plenum.

3. In a hypothermic therapy system as in claim 1, an air filter mounted within said air inlet defined in said housing.

4. A hypothermic therapy control system for supplying heated pressurized air to a patient associated distributor comprising, in combination, a fan having a discharge outlet, an electric heater element within said outlet heating the pressurized air flowing through said discharge outlet to produce a predetermined air temperature, a heated air supply fitting in communication with said outlet, an electronic control circuit operatively connected to said heater element controlling the energization and de-energization thereof, said circuit including an electronic temperature sensor within said discharge outlet operating at a predetermined voltage sensing the air temperature within said outlet, a switch manually adjustable to a predetermined reference value to selectively energize said heater element to maintain said predetermined air temperature as sensed by said sensor, first heater element de-energizing means controlled by said sensor de-energizing said heater element upon said predetermined air temperature being exceeded by a predetermined value, and sensor sensing means sensing the operating voltage of said sensor to sense the operability of said sensor, said sensor sensing means de-energizing said heater element upon said sensor malfunctioning.

5. In a hypothermic therapy control system as in claim 4, said control circuit including alarm means, said sensor sensing means activating said alarm means upon said sensor malfunctioning.

6. In a hypothermic therapy control system as in claim 5, said alarm means including an audio frequency generator emitting sequential audio signals of differing frequency.

7. In a hypothermic therapy control system as in claim 5, said alarm means including a light.

8. In a hypothermic therapy control system as in claim 4, said control circuit including a second heater element de-energizing means de-energizing said heater element at a preselected air temperature in the event said first heater element de-energizing means fails to de-energize said heater element upon said predetermined air temperature being exceeded by said predetermined value.

9. A hypothermic therapy control system for supplying heated pressurized air to a patient associated distributor comprising, in combination, a fan having a discharge outlet, an electric heater element within said outlet heating the pressurized air flowing through said discharge outlet to produce a predetermined air temperature, a heated air supply fitting in communication with said outlet, an electronic control circuit operatively connected to said heater element controlling the energization and de-energization thereof, said circuit including an electronic temperature sensor within said discharge outlet sensing the air temperature within said outlet, a switch manually adjustable to a predetermined reference value to selectively energize said heater element to maintain said predetermined air temperature as sensed by said sensor, first heater element de-energizing means controlled by said sensor de-energizing said heater element upon said predetermined air temperature being exceeded by a predetermined value, and sensor sensing means sensing the operability of said sensor, said sensor sensing means de-energizing said heater element upon said sensor malfunctioning, said control circuit including self-testing circuitry, said self-testing circuitry including a self-testing cycle initiation switch, said self-testing circuitry energizing said heater element causing said heater element to heat the air to a temperature exceeding said air predetermined temperature activating said first heater element de-energizing means.

10. A hypothermic therapy control system for supplying heated pressurized air to a patient associated distributor comprising, in combination, a fan having a discharge outlet, an electric heater element within said outlet heating the pressurized air flowing through said discharge outlet to produce a predetermined air temperature, a heated air supply fitting in communication with said outlet, an electronic control circuit operatively connected to said heater element controlling the energization and de-energization thereof, said circuit including an electronic temperature sensor within said discharge outlet sensing the air temperature within said outlet, a switch manually adjustable to a predetermined reference value to selectively energize said heater element to maintain said predetermined air temperature as sensed by said sensor, first heater element de-energizing means controlled by said sensor de-energizing said heater element upon said predetermined air temperature being exceeded by a predetermined value, and sensor sensing means sensing the operability of said sensor, said sensor sensing means de-energizing said heater element upon said sensor malfunctioning, said control circuit including a second heater element de-energizing means de-energizing said heater element at a preselected air temperature in the event said first heater element de-energizing means fails to de-energize said heater element upon said predetermined air temperature being exceeded by said predetermined value, said control circuit including self-testing circuitry, said first heater element de-energizing means including a triac and said second heater element de-energizing means including a relay.

11. A hypothermic therapy control system for supplying heated pressurized air to a patient associated distributor comprising, in combination, a fan having a discharge outlet, an electric heater element within said outlet heating the pressurized air flowing through said discharge outlet to produce a predetermined air temperature, a heated air supply fitting in communication with said outlet, an electronic control circuit operatively connected to said heater element controlling the energization and de-energization thereof, said circuit including an electronic temperature sensor within said discharge outlet sensing the air temperature within said outlet, a switch manually adjustable to a predetermined reference value to selectively energize said heater element to maintain said predetermined air temperature as sensed by said sensor, first heater element de-energizing means controlled by said sensor de-energizing said heater element upon said predetermined air temperature being exceeded by a predetermined value, and sensor sensing means sensing the operability of said sensor, said sensor sensing means de-energizing said heater element upon said sensor malfunctioning, said control circuit including a second heater element de-energizing means de-energizing said heater element at a preselected air temperature in the event said first heater element de-energizing means fails to de-energize said heater element upon said predetermined air temperature being exceeded by said predetermined value, said control circuit including self-testing circuitry, said self-testing circuitry including a self-testing cycle initiation switch, said self-testing circuitry energizing said heater element causing said heater element to heat the air to a temperature exceeding said preselected air temperature activating said second heater element de-energizing means.

12. In a hypothermic therapy control system as in claim 11, said self-testing circuitry including means deactivating the self-testing cycle if excessive air temperature results form the temperature overheating during the self-testing cycle.

* * * * *

UNITED STATES PATENT OFFICE
CERTIFICATE OF CORRECTION

Patent No. 5,300,098          Dated April 5, 1994

Inventor(s) Thomas H. Phlipot

It is certified that error appears in the above-identified patent and that said Letters Patent is hereby corrected as shown below:

On the title page, in the upper left corner, "Philipot" should read -- Phlipot --.

On the title page, item [75], the identification of the inventor "Thomas H. Philipot" should read -- Thomas H. Phlipot --.

Column 12, line 25, "form" should read -- from --.

Signed and Sealed this

Ninth Day of August, 1994

Attest:

BRUCE LEHMAN

Attesting Officer        Commissioner of Patents and Trademarks